Sept. 16, 1952 W. B. CLARKE Plant Pat. 1,128
LILAC PLANT
Filed Sept. 19, 1951
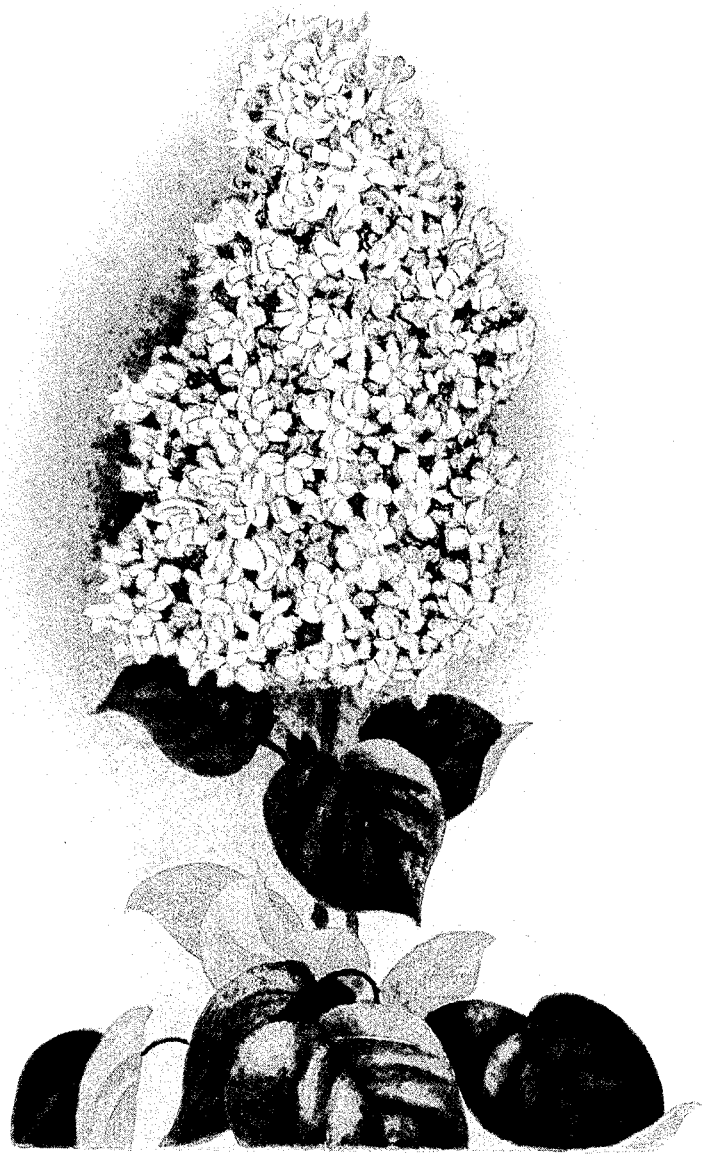
WITNESS
Addison E. Avery
INVENTOR
WALTER B. CLARKE,
by Kummler & Kummler & Shaw,
ATTYS.

Patented Sept. 16, 1952

Plant Pat. 1,128

UNITED STATES PATENT OFFICE 1,128

LILAC PLANT

Walter Bosworth Clarke, San Jose, Calif., assignor to W. B. Clarke & Co., a corporation of California Application September 19, 1951, Serial No. 247,329

1 Claim. (Cl. 47—60)

The present discovery relates to a new and distinct variety of *Syringa vulgaris* plant, occurring as a seedling resulting from a cross made at my nurseries at San Jose, California, between an unknown pollen parent and the seed parent named "Lilac Alice Eastwood" (unpatented). This new variety is the result of definite breeding efforts carried on by me and my associates since 1931. The plant as herein disclosed was first selected for test on April 15, 1949. It has been asexually reproduced at San Jose, California by budding and its characteristics appear to be permanently fixed.

This new variety is distinct from its parents and from any other lilac variety that I have ever seen or tested.

The combination of coloring and the contrast between its deep ruddy mauve buds and nearly white flowers is decidedly unusual and unique. The buds are deep Fuchsia purple and the open flowers are the palest possible lavender which seems to be pure white by contrast with the unopened buds. The reverses or backs of the flowers are pale Fuchsia purple but after the flowers have fully opened these do not show, except on close examination.

Flowers bloom freely, opening just after midseason or rather late, and stay in bloom about three weeks. Fragrance is good. The florets are double but not crowded in the thyrses. The clusters are of medium size and are borne either singly or in forked pairs, well above the foliage on long shoots, which characteristic makes them particularly well adapted for cutting. In general plant structure, this new variety is similar to the well-known *Syringa vulgaris*. Growth is vigorous and erect, not widespreading.

There is a sufficient quantity of foliage which forms a pleasing contrast to the coloring of the buds and flowers. The bush is somewhat slender and grows to a height of from six to eight feet.

The accompanying painting shows the approximate shape of a single panicle, and its distinctive coloring.

The colors are as follows:

*Buds.*—Fuchsia purple, plate 28 to 28/3, Horticultural Colour Chart of The British Colour Council; or Maerz and Paul Dictionary of Color, Plate 51–K–7.

*Open flower.*—Maerz and Paul, plate 49–A–2.

*Reverse of flowers.*—Pale Fuchsia purple.

This new variety of lilac is easily distinguished from other varieties by its unique and remarkable combination of colors.

Having thus disclosed the invention, I claim:

A new and distinct variety of *Syringa vulgaris* plant with features in combination substantially as shown and described, characterized by the Fuchsia mauve coloring of its buds progressively changing into the distinctive nearly white pale lavender of the full-blown flowers.

WALTER BOSWORTH CLARKE.

No references cited.